(12) United States Patent
Stone et al.

(10) Patent No.: US 7,959,680 B2
(45) Date of Patent: Jun. 14, 2011

(54) METHOD AND APPARATUS FOR PERFORMING A SHOULDER IMPLANT PROCEDURE

(75) Inventors: Kevin T Stone, Winona Lake, IN (US); Brian K Berelsman, Warsaw, IN (US); Jason M Shultz, Liberty Township, OH (US); Nathan A Winslow, Warsaw, IN (US); Russell M Parrott, Winona Lake, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 473 days.

(21) Appl. No.: 11/346,543

(22) Filed: Feb. 2, 2006

(65) Prior Publication Data

US 2007/0179624 A1  Aug. 2, 2007

(51) Int. Cl.
*A61F 2/40* (2006.01)
(52) U.S. Cl. .................. 623/19.13; 623/19.11
(58) Field of Classification Search ............. 623/19.11, 623/19.12, 19.13, 22.38
See application file for complete search history.

(56) References Cited

U.S. PATENT DOCUMENTS

| | | |
|---|---|---|
| 3,694,820 A | 10/1972 | Scales et al. |
| 3,803,641 A | 4/1974 | Golyakhovsky |
| 3,842,442 A | 10/1974 | Kolbel |
| 4,042,980 A | 8/1977 | Swanson et al. |
| 4,045,825 A | 9/1977 | Stroot |
| 4,045,826 A | 9/1977 | Stroot |
| 4,106,130 A | 8/1978 | Scales |
| 4,129,903 A | 12/1978 | Huggler |
| 4,550,450 A * | 11/1985 | Kinnett ................. 623/20.11 |
| 4,578,081 A | 3/1986 | Harder et al. |
| 4,693,723 A | 9/1987 | Gabard |
| 4,822,370 A | 4/1989 | Schelhas |
| 4,851,007 A | 7/1989 | Gray |
| 4,919,669 A | 4/1990 | Lannelongue |
| 5,047,060 A | 9/1991 | Henssge et al. |
| 5,358,526 A | 10/1994 | Tornier |
| 5,383,936 A | 1/1995 | Kubein-Meesenburg et al. |
| 5,462,563 A | 10/1995 | Shearer et al. |
| 5,507,819 A * | 4/1996 | Wolf ..................... 623/19.11 |
| 5,580,352 A | 12/1996 | Sekel |
| 6,306,173 B1 | 10/2001 | Masini |

(Continued)

FOREIGN PATENT DOCUMENTS

| | | |
|---|---|---|
| EP | 1336396 | 8/2003 |
| FR | 2578162 | 9/1986 |

OTHER PUBLICATIONS

"Technical Considerations for Implantation of EPOCA Constrained Glenoid" Ralph Hertel, MD, PD, Department of Orthopedic Surgery, Inselpsital, University of Bern, published in EPOCA Newsletter May 14, 2001.

*Primary Examiner* — David Isabella
*Assistant Examiner* — Joshua Levine
(74) *Attorney, Agent, or Firm* — Harness, Dickey (57) ABSTRACT

Disclosed is a set of prosthetic components for use in shoulder replacements. A glenoid component having a base and a plurality of coupling members are disclosed. The coupling members are used to couple the base to at least one of the acromion or coracoid process. A polymer insert which is configured to couple to the base member and articulate with a humeral component is provided.

15 Claims, 12 Drawing Sheets

U.S. PATENT DOCUMENTS

| | | |
|---|---|---|
| 6,340,370 B1 | 1/2002 | Willert et al. |
| 6,416,553 B1 | 7/2002 | White et al. |
| 6,458,161 B1 * | 10/2002 | Gibbs et al. ............ 623/22.32 |
| 2002/0116068 A1 | 8/2002 | McLean |
| 2003/0158605 A1 * | 8/2003 | Tornier ................ 623/19.11 |
| 2004/0220673 A1 | 11/2004 | Pria |
| 2006/0079963 A1 * | 4/2006 | Hansen ................ 623/19.11 |

* cited by examiner

METHOD AND APPARATUS FOR PERFORMING A SHOULDER IMPLANT PROCEDURE

FIELD OF THE INVENTION

The present disclosure relates to a kit of prosthetic components for repair and reconstruction of a portion of a ball-and-socket joint, and more specifically a kit of adapters used to vary the distance between an articulating prosthetic surface and a bone fixation component.

BACKGROUND

The shoulder joint is considered to be one of the most complex joints in the body. The scapula, the clavicle, and the humerus all meet at the shoulder joint. The head of the humerus fits into a shallow socket of the scapula called the glenoid fossa to form a mobile joint. When the joint is articulated, the humeral head moves in the glenoid fossa to provide a wide range of motion. The shoulder joint may suffer from various maladies including rheumatoid arthritis, osteoarthritis, rotator cuff arthropathy, vascular necrosis or bone fracture. If severe joint damage occurs and no other means of treatment is found to be effective, then a total or partial shoulder reconstruction may be necessary.

A shoulder joint prosthesis generally includes the replacement of the ball of the humerus and, optionally, the socket of the shoulder blade with specially designed artificial components. The bio-kinematics, and thus the range of motion in the shoulder vary greatly among prospective patients for reconstructive shoulder surgery. The humeral component typically has a metal shaft or stem with a body portion that is embedded in the resected humerus and a generally hemispherical head portion supported on the stem. The head slidingly engages a glenoid implant on the glenoid fossa. During reconstructive surgery, the components of the prosthesis are matched with the bio-kinematics of the patient in an effort to maintain the natural range of motion of a healthy shoulder joint. Thus, a shoulder prosthesis design must be readily adaptable to a wide range of bio-kinematics for prospective patients.

In this regard, shoulder prostheses are generally available as either unitary structures or modular components. With unitary shoulder prosthesis, a large inventory of differently sized prostheses must be maintained to accommodate the different bone sizes and joint configurations of the prospective patients. With such unitary shoulder prosthesis, the patient is typically evaluated by x-ray to determine the approximate prostheses size needed for reconstruction. A number of differently sized prostheses are selected as possible candidates based upon this preliminary evaluation. Final selection of the appropriately sized prosthesis is made during the surgery.

Modular prostheses systems which reduce the need to maintain large inventories of various sized components are well known in the art. Conventionally, the humeral prosthesis includes two components—a humeral stem component and a spherical head releasably coupled to the stem. Alternately, a three component design is known in which the stem and shoulder are interconnected with an adapter. In either of the two-piece or three-piece designs, a radial offset or angulator inclination of the head relative to the stem is provided in individual components. For example, in the three-piece design, an adapter may be configured with a fixed radial offset of 2 millimeters or an angular inclination of 5 degrees. Different radial offsets or angular inclinations are achieved through the use of different adapters or heads. In this regard, conventional modular shoulder prosthesis kits include multiple redundant components such as adapters and heads to achieve a range of prosthetic options.

While providing an advantage over the unitary design in reducing the number of components needed, a rather large inventory of head components and/or adapter components must be maintained to provide the desired range of geometric configurations with the conventional modular shoulder prostheses. Therefore, there is a need for modular shoulder prostheses which are readily adaptable to provide a range of geometric configurations, i.e. radial offsets, vertical offsets, and angular inclinations while minimizing the number of components required.

SUMMARY OF THE INVENTION

A modular adapter prosthesis kit is provided in accordance with the teachings of the present disclosure. The kit includes a set of coupling members for a glenoid prosthesis, which cooperates with an articulating prosthetic head and fixation component, to provide a range of radial offsets. The coupling members are configured for use with a total shoulder prosthesis to couple the glenoid to one of the acromion or coracoid process of a patient.

A kit of prosthetic components is provided for adjustable rotational offset of a base of an articulating surface for a glenoid. The base can include a superior bearing support member having two coupling mechanisms. The height of the first coupling mechanism determines the rotational offset of the base of the articulating surface. The kit can also include a second adapter having at one more coupling mechanisms. The height of one of the coupling mechanisms also determines the rotational offset between the base of the articulating surface and the base of the coupling mechanism of the second adapter.

The prosthesis kit of the present disclosure provides great flexibility in the adjustment of important bio-kinematic parameters for joint prosthesis systems, while minimizing the number of components required for the modular system. These and other features of the present disclosure will become apparent from the description and especially taken in conjunction with the accompanying exemplary drawings.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiment(s) is merely exemplary in nature and is in no way intended to limit the invention, its application, or uses.

Figure 1:
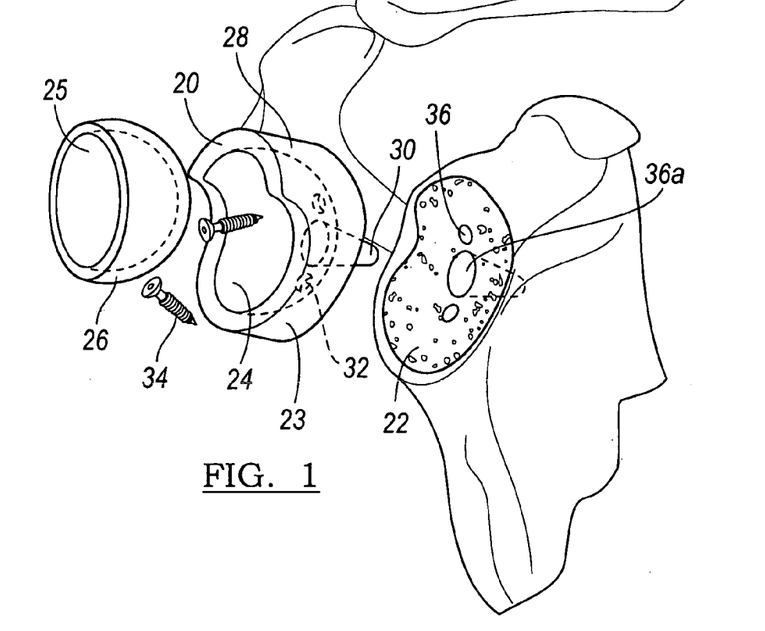
FIG. 1 represents an exploded view of the prosthetic according to one embodiment.

FIG. 1 represents a glenoid prosthetic 20 according to the teachings of the various embodiments. The glenoid prosthetic 20 is coupled to a prepared and resected glenoid 22. The prosthetic 20 has a bearing support member 23 having a spherical cup bearing surface 24 and a bearing cup 26. The support member 23 further has a constraining wall 28, which is generally positioned on a superior side of the bearing support 23.

Figure 2:
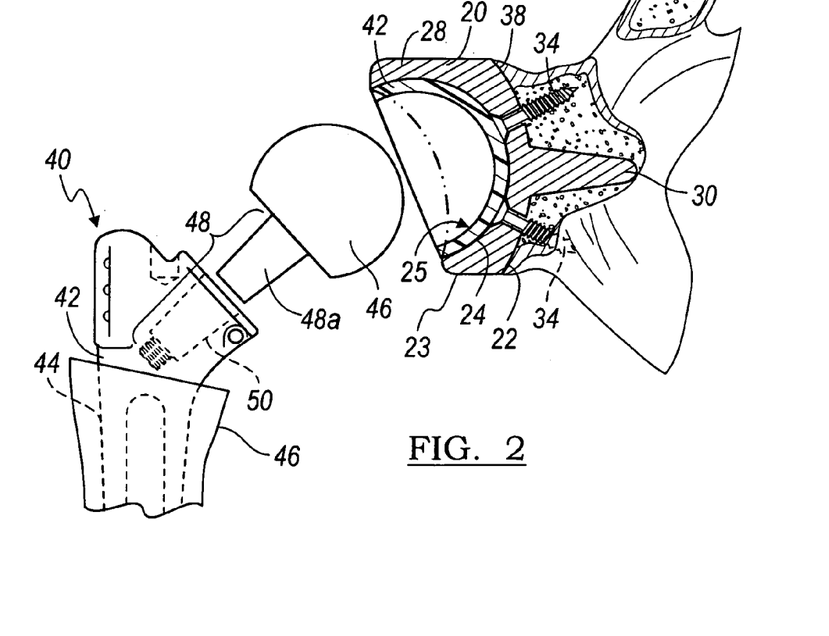
FIG. 2 represents a cross-sectional view of an implant shown in FIG. 1.

As shown in FIG. 2, the bearing support 23 defines the generally concave bearing surface 24, which supports the bearing cup 26. The bearing cup 26 has a concave bearing surface 25, which is configured to couple to a humeral prosthetic 40. The glenoid prosthetic is coupled to the resected glenoid 22 at a coupling surface 38, which has a first convex radius. The cup bearing surface has a second concave radius, which can have a valve generally less than the first concave radius. Defined in the bearing support member 23 is a plurality of apertures 32, which function to accept a plurality of bone engaging fasteners 34.

The glenoid prosthetic 20 is configured to interface with the humeral prosthetic 40, which has a fixation stem 42 and a head 46. Disposed between the head 46 and the fixation stem 42 is a fixation mechanism 48, which is configured to be coupled to a coupling taper 50 defined by the fixation stem 42. As is known, the fixation stem 42 is configured to be implanted into the medullary canal 44 of the resected humerus 46.

FIG. 2 shows a side sectional view of the prosthetic 20 coupled to the resected glenoid 22. The prosthetic 20 is coupled to the resected glenoid 22 using a coupling stem 30 implanted into an aperture 36a within the prepared glenoid. Additionally, a pair of bone fixation screws 34 are driven through the apertures 32 formed in the bearing support 23. In this regard, the screws 34 are driven generally skew to an axis of the stem 30 to augment fixation to the glenoid 22.

Figure 3:
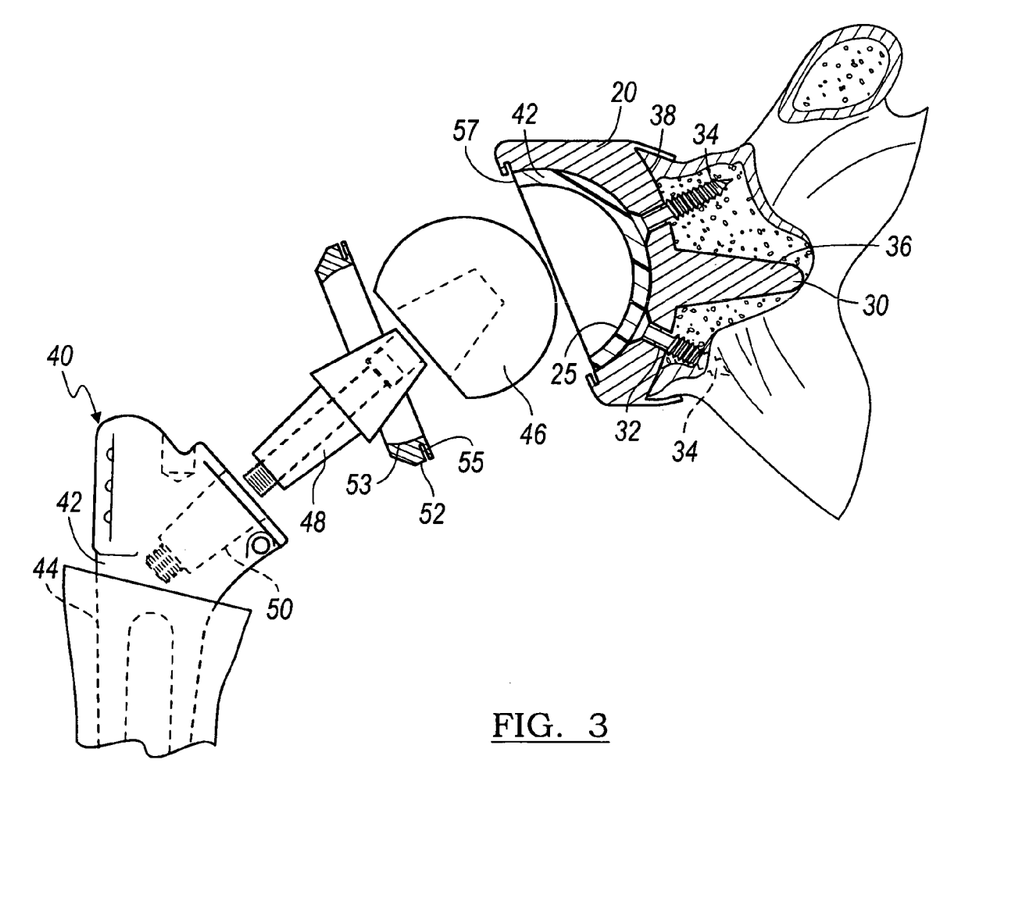
FIG. 3 represents an alternate shoulder prosthetic.

FIG. 3 represents a glenoid prosthetic 20 configured to constrain movement of the humeral head 46. In this regard, the prosthetic 20 can have a constraining ring 52, which locks to the bearing support 23 using a snap-ring (now shown). The constraining ring 52 has a ring bearing surface 53, which is configured to function as an articulating bearing surface, with respect to the moving humeral head 46. The ring 52 further has a ring coupling surface 55, which is configured to be fixably coupled to a bearing support ring coupling surface 57.

Figure 4:
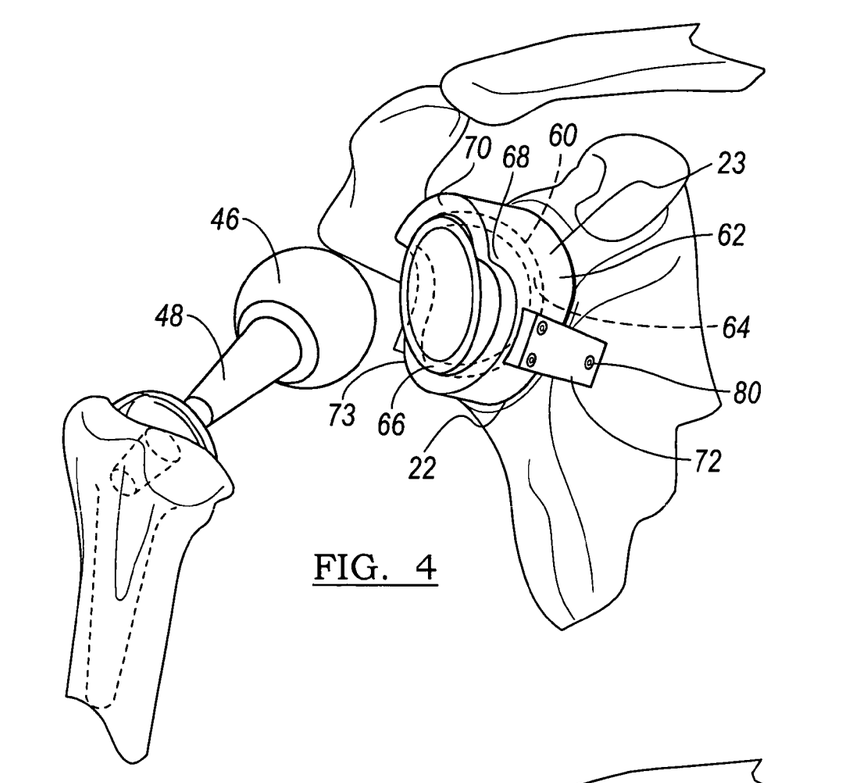
FIGS. 4 and 5 represent alternate shoulder prosthetics.
Figure 5:
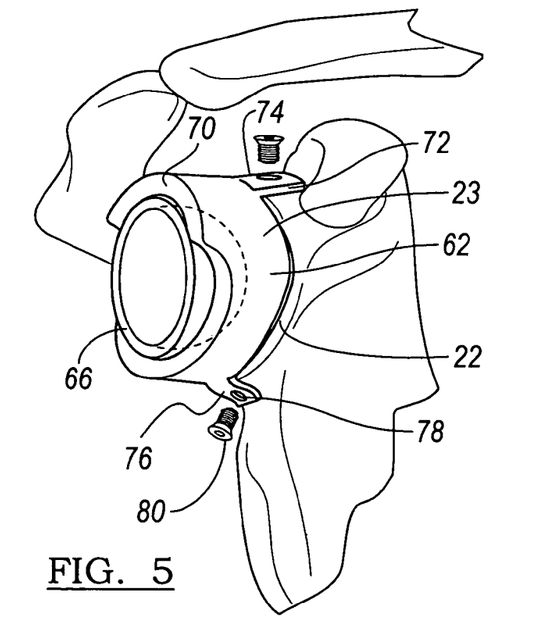

FIGS. 4 and 5 represent an alternate glenoid prosthetic 60 having augmented fixation. To this end, the glenoid prosthetic 60 has additional exterior fixation flanges 72 configured to fix the bearing support 23 to the scapula. These flanges 72 can be integral with or coupled to an exterior surface of the bearing support 23.

The flanges 72 define apertures 78 for accepting fixation screws 80. While the flanges 72 can be placed anywhere radially about the bearing support member 23, it is envisioned that pairs of flanges 72 can be placed radially opposite to each other. The flanges 72 can be elastically or plastically deformed to conform to the shape of the scapula about an exterior surface of the support member 23. It is further envisioned that the flanges 72 can be placed at anterior and posterior positions, or superior 74 and inferior positions 76.

The bearing support member 23 has a superior ledge 70, which functions to reduce movement of the head 46 in the superior 74 direction. The bearing side support walls 68 have a cut out section 73, which allows for extended movement of the humeral head 46 without interference of the humeral coupling member 48 with the bearing support 23 or bearing 66.

Figure 6:
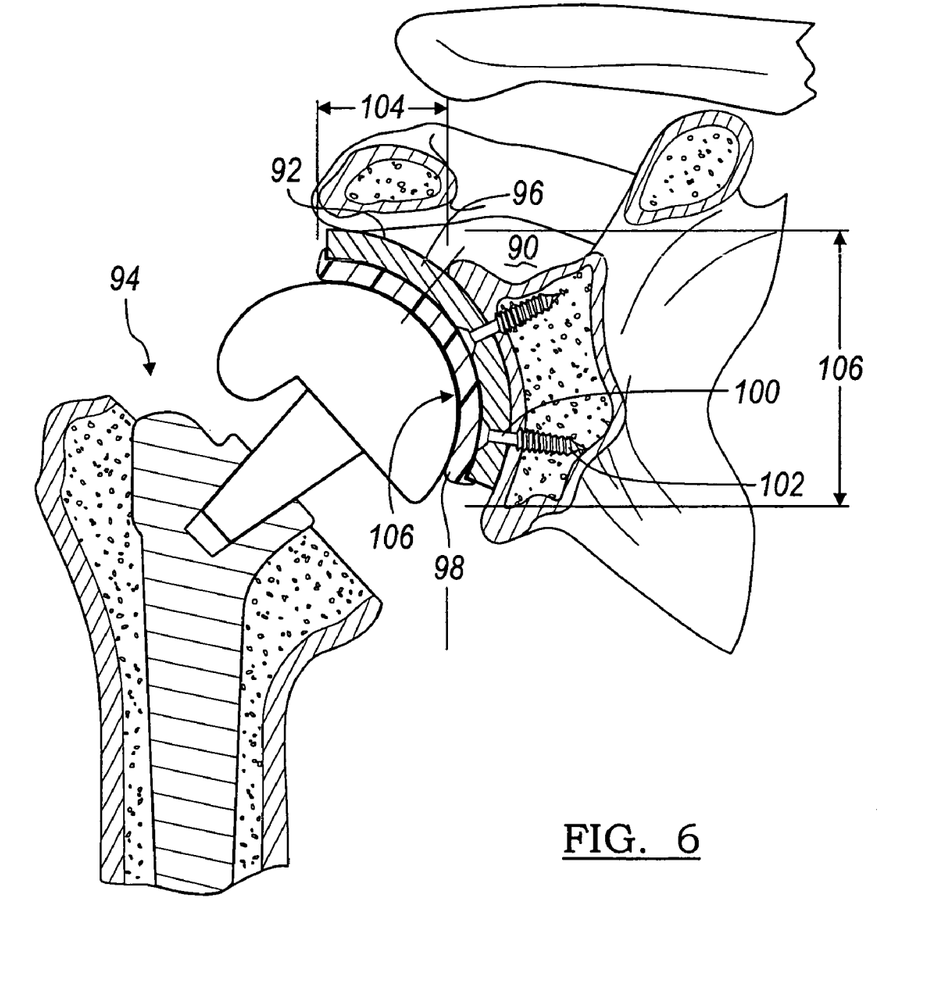
FIG. 6 represents a side view of an alternate glenoid prosthetic.

FIG. 6 represents an alternate shoulder prosthetic 90. The prosthetic 90 has a glenoid member 92 and a humeral component 94. The glenoid member 92 has a glenoid bearing support 96 and a glenoid bearing member 98. The glenoid bearing support 96 defines a plurality of support apertures 100, which function with the fixation screws 102 to couple the prosthetic glenoid 90 to the prepared glenoid as previously described.

The glenoid bearing support 96 and glenoid bearing 98 define a generally constant radius of curvature. In this regard, the glenoid bearing support 96 and glenoid bearing 98 have first and second portions 104 and 106. The first portion 104 is generally placed perpendicular to the surface defined by the natural glenoid. Further, the first portion is generally superiorly located with respect to the second portion 106 and functions to resist the superior movement of the head 46 of the humeral prosthetic 94.

Figure 7:
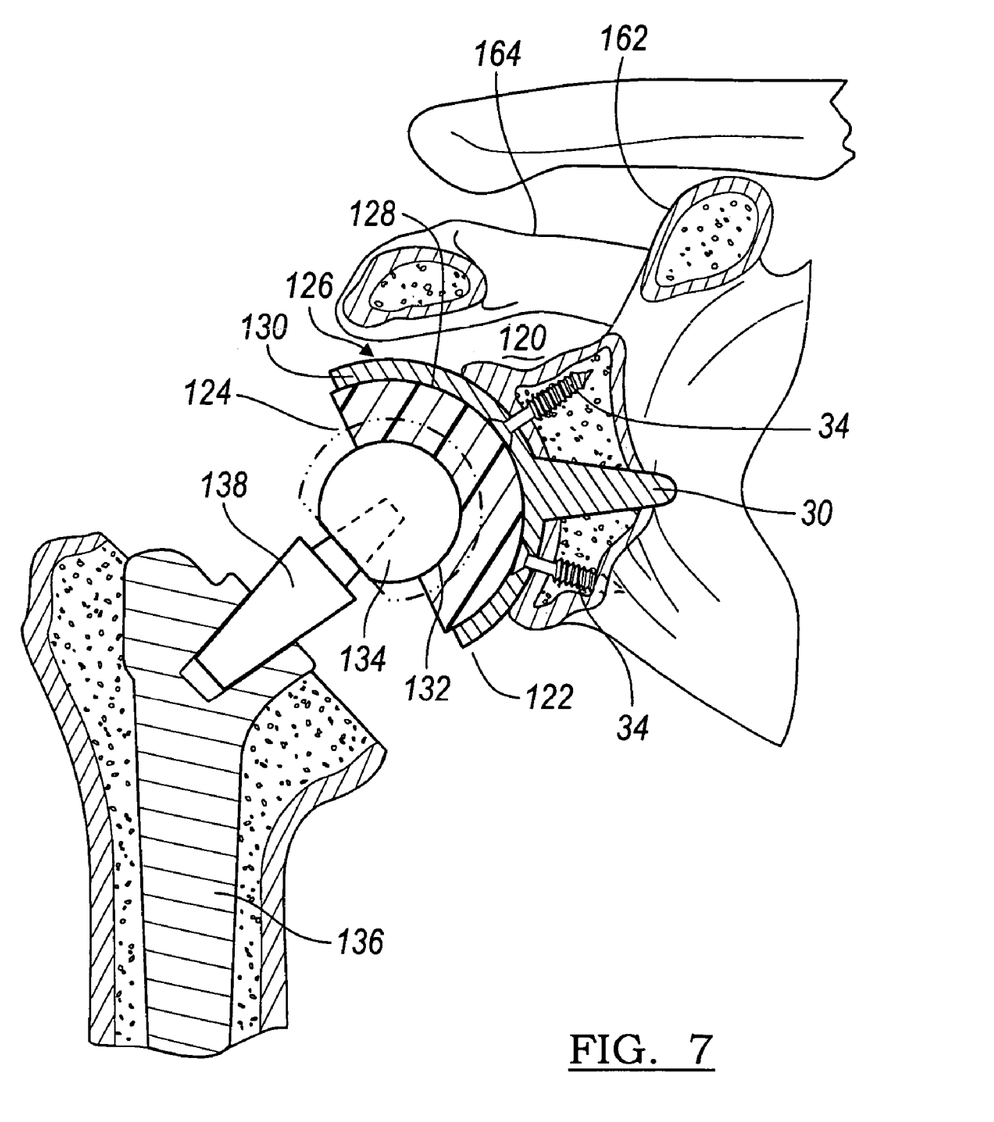
FIG. 7 represents a side view of an alternate glenoid prosthetic.

FIG. 7 represents an alternate shoulder prosthetic 120. The prosthetic 120 has a glenoid bearing support 122 and a glenoid bearing 124. The glenoid support 122 has a first coupling surface 126, which is configured to be mated to a prepared glenoid as previously described. In this regard, the bearing support coupling 126 surface defines a plurality of apertures for accepting of bone engaging fasteners 34. The bearing support coupling surface 126 further has a support stem 30. The bearing support 122 further has a bearing support bearing surface 128, which is configured to be coupled to the convex bearing exterior surface 130 of bearing 124. The bearing 124 has a concave surface having a radius of less than about 32 mm. This radius allows for the proper interaction between the bearing surface 132 and an exterior surface of the prosthetic humeral head 134.

Figures 8, 9:
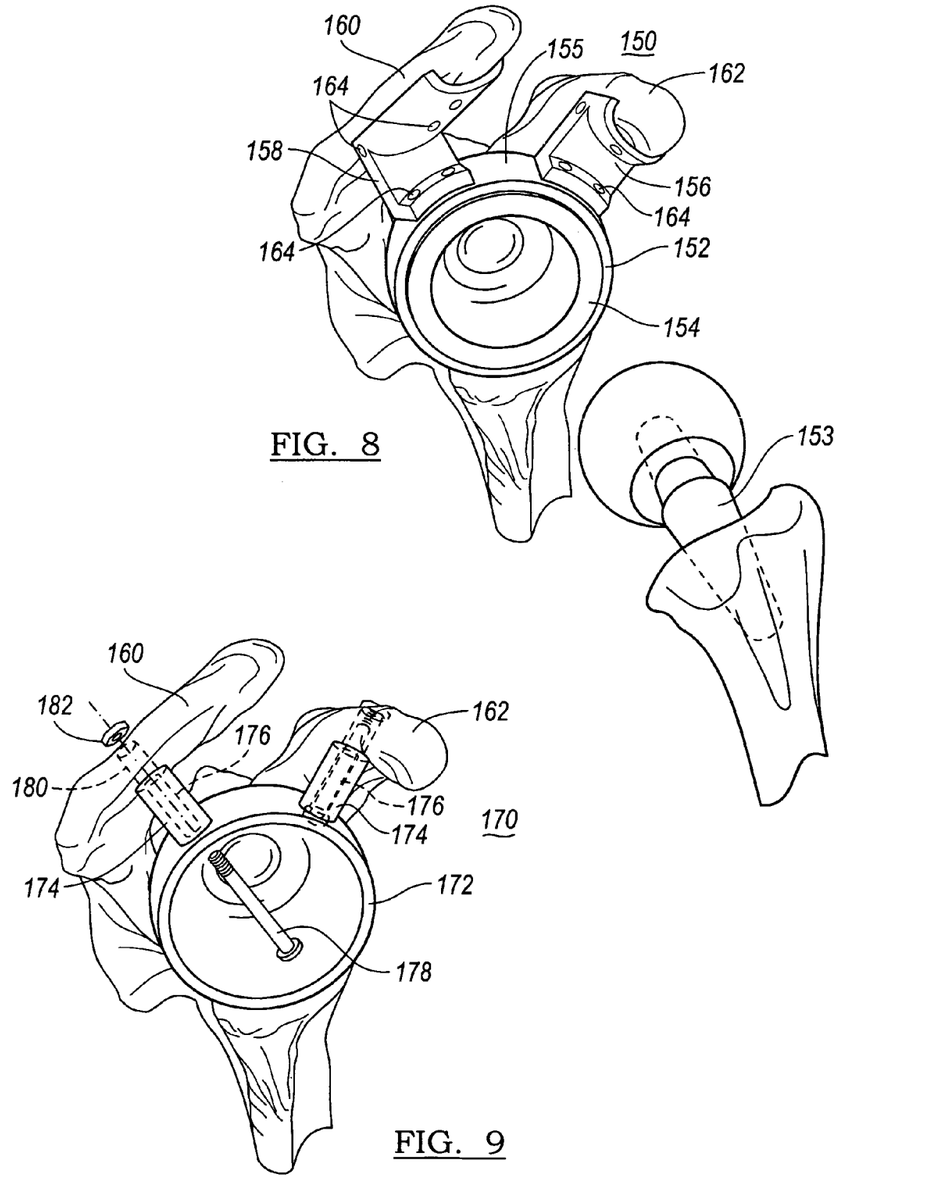
FIG. 8 represents a perspective view of a constrained glenoid according to the present teachings.
FIG. 9 represents the coupling of an alternate constrained glenoid according to the present teachings.

FIGS. 8 and 9 represent an alternate glenoid prosthetic 150. The glenoid prosthetic 150 has a glenoid bearing support or base 152, which can be coupled to a prepared glenoid as previously described. The glenoid bearing support 152 is configured to accept a bearing insert 154, which is configured to mate with a humeral prosthetic 153, as previously shown and described above.

Disposed at superior locations of an external surface 155 of the glenoid bearing support 152 is a pair of flanges 156 and 158. These flanges are fixedly coupled to the exterior surface 155 using a pair of fixation elements 164. The flanges are configured to span the gap between the exterior surface 155 of the glenoid bearing support 152 and the acromion process 160 or the coracoid process 162. Further, the flanges 156 and 158 are fixably coupled to the acromion process 160 and coracoid process 162 using a pair of bone fixation screws 164, which are disposed through a pair of apertures defined within the flanges 156 and 158.

With reference to FIG. 9, the pair of flanges 156 and 158 can take the form of tubular members 174. These tubular members 174 defined apertures 176, which function to accept threaded fasteners 178 disposed therethrough. The fasteners 178 are further disposed through holes 180 defined in the acromion process 160 and coracoid process 162. The end of the fasteners 178 can be fixed using a secondary fastener, such as nut 182 or can be embedded into the acromion or coracoid process 160, 162.

FIGS. 10A-13 show an alternate glenoid prosthetic 190. The alternate glenoid prosthetic 190 has a glenoid bearing support 192 and a glenoid bearing member 194. The glenoid bearing support 192 has a superior support ledge 196, which defines a plurality of holes 198. As described below, these holes 198 function to accept bone fixation fasteners 200 to allow the coupling of the superior support ledge 196 to the acromion process 160 and/or the coracoid process 162. These fasteners can be bone fixation screws or the threaded bolts shown in FIG. 9.

Figure 10A:
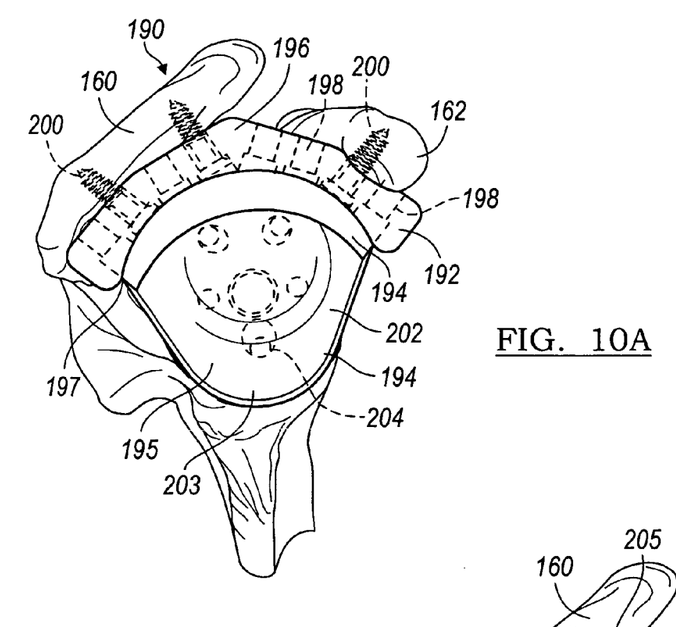
FIGS. 10A and 10B represent an alternate partially constrained glenoid prosthetic.
Figure 10B:
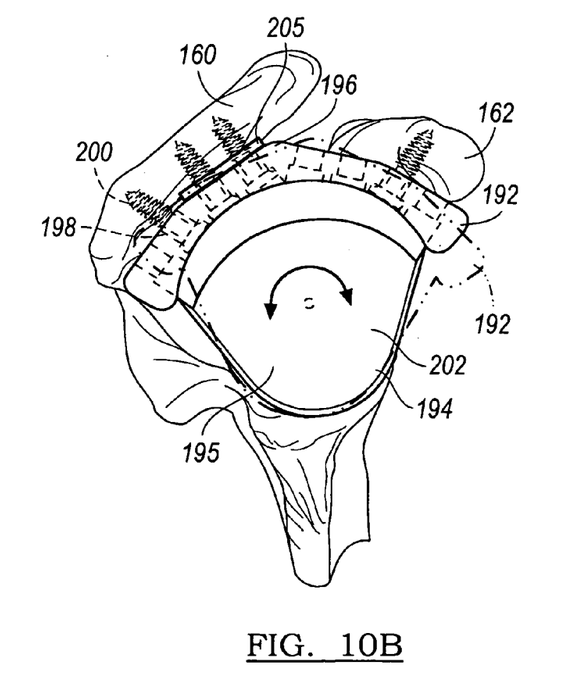

The glenoid bearing support 192 further has a glenoid bearing base or support tray 202, which defines a plurality of apertures 204 that function to accept bone fixation screws to couple the glenoid bearing support to the resected glenoid. The glenoid bearing 194 has a tray bearing surface 195 and a superior support ledge interfacing surface 197.

As shown in FIGS. 10A-10E, the prosthetic glenoid 190 has a bearing support 192 configured to be coupled to the glenoid surface. Disposed between the bearing support 192 and the acromion process or the coracoid process is at least one coupling member 200. The coupling member 200 functions to fixably couple the base to either one of the acromion 160 or coracoid process 162.

The bearing support 192 defines either a spherical or flat insert support surface 197. The bearing support 192 further can have a superior support structure or ledge 196 which defines a plurality of apertures 198 configured to accept the coupling members 200. These apertures 198 can either be threaded or unthreaded or can be elongated.

The bearing support 192 can have a generally L-shaped cross-section. The bearing support 192 further defines a plurality of through bores 204 which are configured to accept bone engaging fasteners. It is envisioned that the apertures 204 can be radially spaced about a centrally located bore 212. Further, the apertures 204 can be skew from the centrally located bore 212.

Figure 10C:
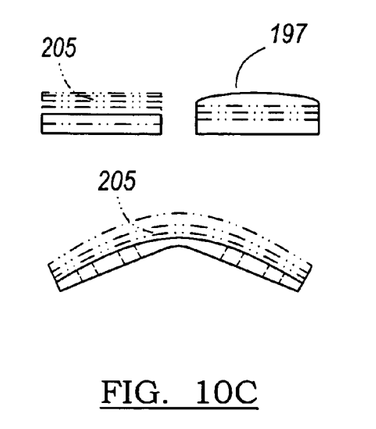
FIG. 10C represents optional spacer elements for use with the glenoid prosthetic, as shown in FIGS. 10A and 10B.
Figure 10D:
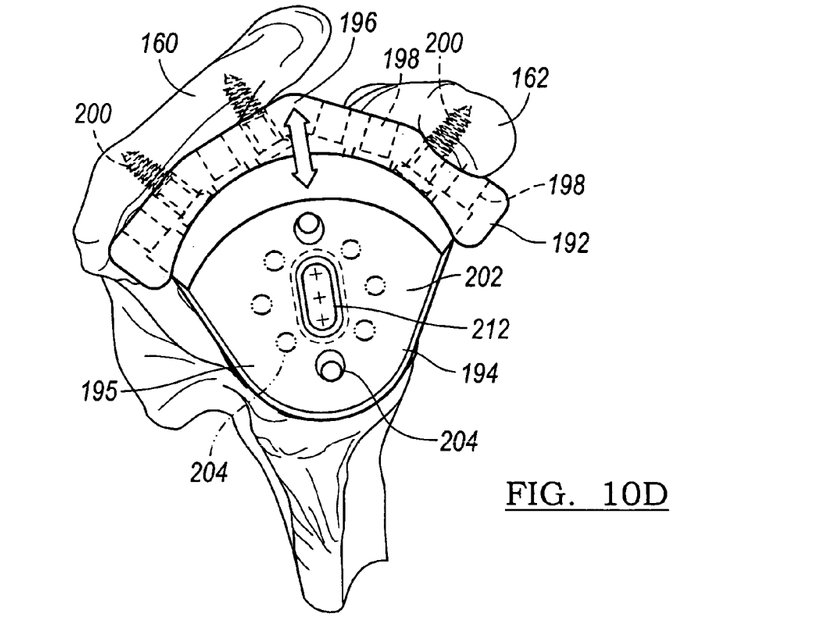
FIGS. 10D and 10E represent the coupling of a glenoid base to a prepared scapula.
Figure 10E:
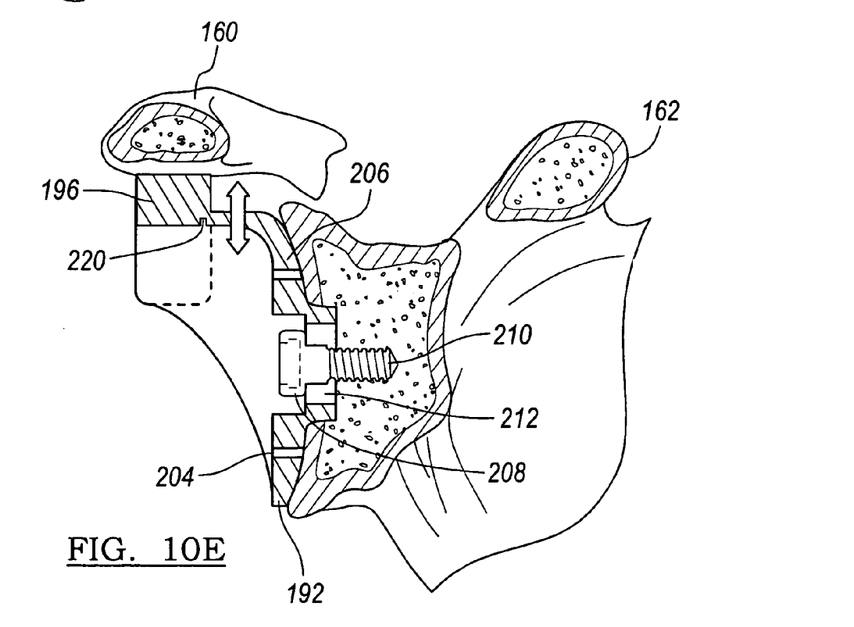

The coupling member 200 can be a threaded member configured to engage the bone of the acromion 160 or coracoid process 162. The threaded coupling member 200 can either be tapered to form a bone engaging screw or can be a bolt configured to couple the superior support structure to a threaded nut (see FIGS. 12 and 13). The coupling member 200 can have a spacer member 205 configured to support the coupling member. In this regard, the spacer member 205 is configured to fill the space between the bearing support 192 or superior support structure 196 and the acromion 160 or coracoid process 162. It is envisioned that the spacer 205 can have varying exterior shapes to engage the surfaces. Measurements by a treating physician can be made using appropriately sized templates. In this regard, the spacer 205 can have a flat surface configured to engage a superior support structure 196. Additionally, it is envisioned that the spacer 205 can have any surface geometry which allows the interface with the support structure 196, or a porous coating to allow boney ingrowth.

As seen in FIGS. 10B-10E, the base can be rotated about the centrally located fixation member and translated to conform to anatomical requirements. After fixing the base to the resected glenoid, the polymer bearing can be inserted. In this way, spacers 205 can be used to augment and support the coupling mechanism 200 to reduce the likelihood of joint dislocations in particular patients.

Figure 11:
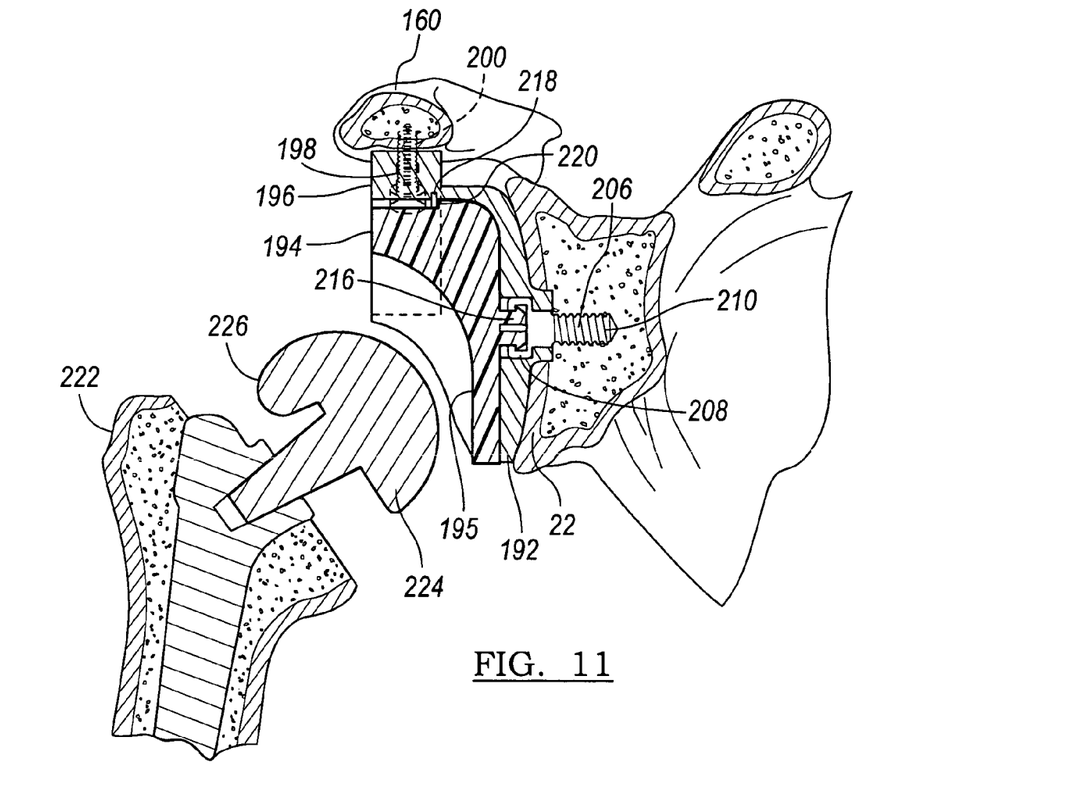
FIG. 11 represents a cross-sectional view of the shoulder shown in FIG. 10.
Figure 12:
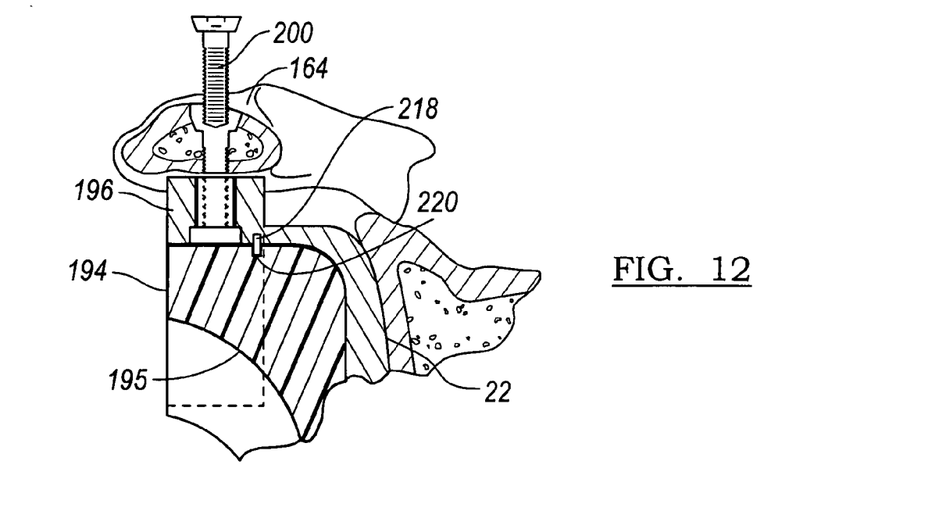
FIG. 12 represents a close up of the insertion of the acromion screw into the glenoid component shown in FIG. 11.

FIGS. 11 and 12 depict side cross-sectional views of the shoulder prosthetic shown in FIGS. 10A-10E. The glenoid fixation component 206 couples the glenoid bearing support 192 to the resected glenoid 22. The glenoid fixation component 206, found on threaded fixation member 210, is positioned through a fixation aperture 208 defined in the glenoid support tray 192. A locking mechanism 216 can be used to couple the glenoid bearing 194 to an aperture formed in the glenoid fixation component 206. As shown in FIG. 11, a fixation member 210 is seated within a counterbore within the glenoid bearing support tray 192. The threaded fixation member 210 is coupled to an aperture formed in the prepared glenoid 22.

As seen in FIG. 11, locking mechanism 214, disposed between the superior support ledge 196 and the glenoid bearing member 194 is a snap locking member 218. The snap locking member 218 is located within a notch 220 defined by the superior support ledge 196 and the glenoid bearing 194. The bearing surface 195 of the glenoid bearing 194 is configured to slidably accept the articulating surface of the humeral head 224 of the humeral prosthetic 222. As best shown in FIG. 11, the humeral head 224 can have an extended articulating surface 226 configured to interface with a superior portion of the bearing surface 195 of the bearing support 194.

Figure 13:
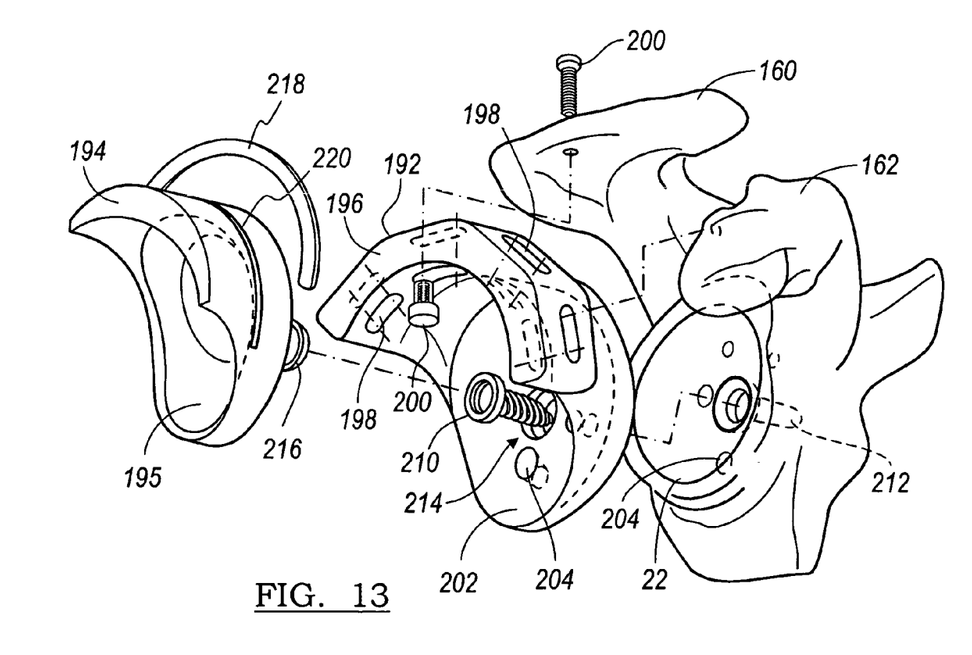
FIG. 13 represents an exploded view of the glenoid shown in FIG. 11.

FIG. 13 represents an exploded perspective view of the prosthetic shown in FIGS. 10A-12. The glenoid is prepared by first forming the center hole followed by reaming the glenoid surface. As can be seen after preparing the glenoid 22, a plurality of holes 204 are formed after the positioning of the support within the resected glenoid 22.

The internally threaded sleeve 212 can be positioned within one of the apertures 204 to accept the coupling fastener 210. Optionally, the flange can be coupled using a fixation screw. As previously described, the apertures 204 can be located askew to the axis of the coupling fastener 210. After coupling the glenoid bearing support 192 to the resected glenoid 22, a plurality of holes are disposed through the acromion process 160 and coracoid process 162 using the holes in the superior support ledge 196 as a drilling guide. The fasteners can then be either directly coupled to the acromion process 160 or coracoid process 162 or a two piece fastener 200 can be used. Member 200 can have a detail of a square, hex or other geometry to prevent rotation of the internally threaded member 200 during tightening. At this point, the polymer bearing 194 is coupled to the glenoid bearing support 192 using the snap fastener 218 and locking tab 216.

Referring generally to FIGS. 14A-16, disclosed is a shoulder prosthetic 220 utilizing an inferior support bracket 224. The prosthetic 220 is coupled to a resected glenoid using a fixation peg 222. The inferior support bracket 224 is used to stabilize the glenoid in situations where there is degradation of the underlying resected glenoid material to enhance fixation and support.

Figure 14A:
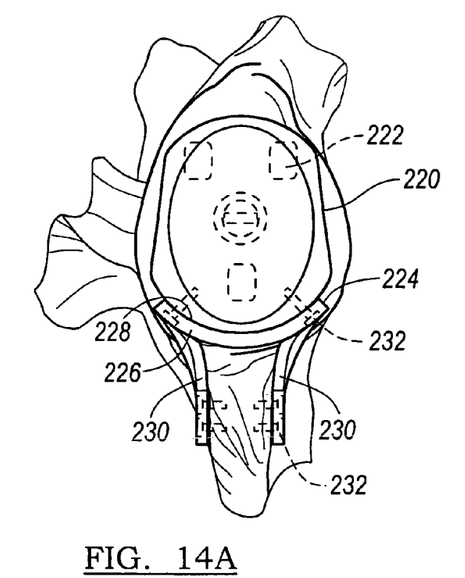
FIGS. 14A-14C represent a support bracket for the glenoid prosthetic.
Figure 14B:
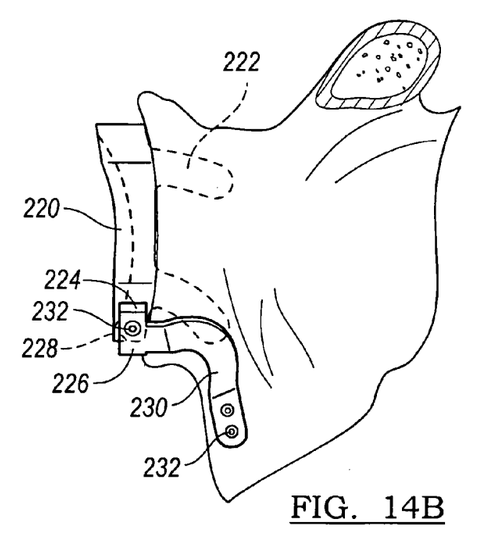
Figure 14C:
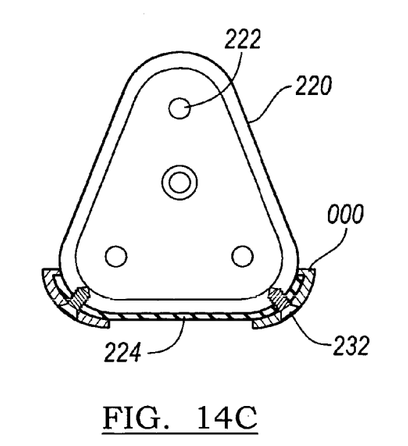

The inferior support bracket 224 is formed of a curved support member 226, which supports a bearing surface 228 of the glenoid. A pair of support flanges 230 are coupled to the curved support member 226 and function to allow the coupling of the inferior support bracket to a metal shell or base using a plurality of fixation members 232.

Figure 15:
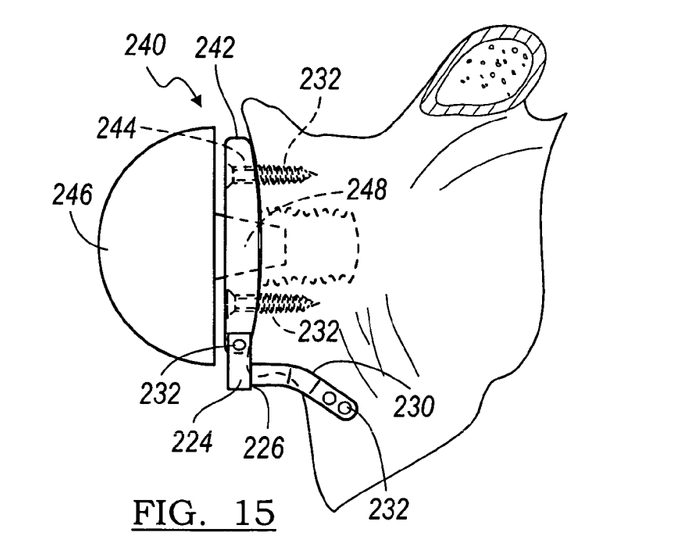
FIGS. 15 and 16 show the use of the support bracket with a reverse shoulder glenoid component.
Figure 16:
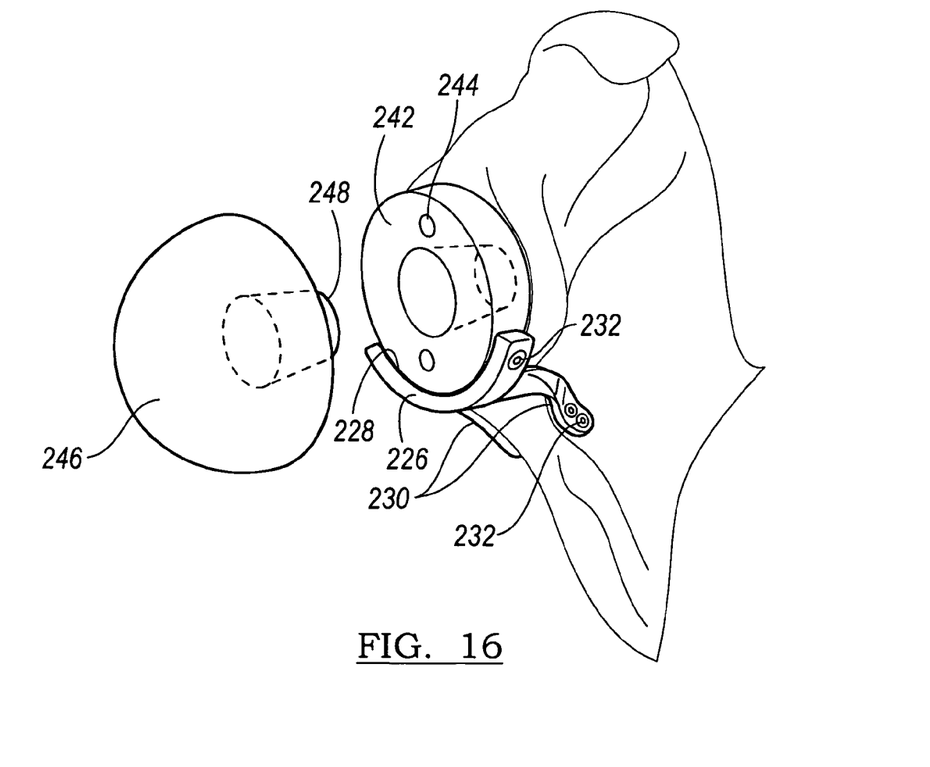

As best shown in FIGS. 15 and 16, the inferior support bracket 224 can be used to support a glenoid component in a reverse shoulder prosthetic 240. The reverse shoulder prosthetic 240 utilizes a base member 242, which is coupled to the resected glenoid using a plurality of bone fixation screws 232 disposed through apertures 244 in the base 242. The head 246 is coupled to the base using a coupling member 248. As described with respect to the glenoid prosthetic in FIGS. 14A-14C, the inferior support bracket 224 has a curved support member 226, which functions to interface with a curved bearing surface 228 on the base 242 of the reverse shoulder prosthetic 240. The pair of support flanges 230 are used to couple the inferior support bracket 224 to the scapula.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A method of implanting an implant comprising:
   preparing a glenoid surface;
   coupling a glenoid base having a generally L-shaped cross-section formed of a superior ledge portion and support tray, to the prepared glenoid surface;
   at least one of translating or rotating the glenoid base to engage the superior ledge portion with at least one of the acromion or coracoid process, after coupling a glenoid base to the prepared glenoid surface;
   measuring a distance between the superior ledge portion and at least one of the acromion or coracoid process;
   placing a spacer defining an aperture between the superior ledge portion and at least one of an acromion or coracoid process of a patient;
   coupling the spacer to the glenoid base;
   coupling the glenoid base to the spacer and to at least one of an acromion or coracoid process by passing a fastener through the aperture and into the bone and
   after coupling a glenoid base to the prepared glenoid surface, fixing a bearing component having a generally L-shaped cross-section having a bearing superior ledge and a concave ledge articulating surface to the glenoid base so as to couple the bearing superior ledge to the superior ledge portion.

2. The method according to claim 1 further including choosing the spacer size based upon the measurement.

3. The method according to claim 2 further including removably coupling the spacer between the glenoid base and at least one of the acromion or coracoid process.

4. The method according to claim 1 further comprising measuring the distance between glenoid base and one of the acromion or coracoid process.

5. The method according to claim 1 wherein fixing a bearing component to a glenoid base is fixing a bearing component to a glenoid base after coupling the glenoid base through an aperture defined in the spacer.

6. A method of implanting an implant comprising:
   coupling an L-shaped glenoid base having a superior ledge member and a support tray to a prepared glenoid surface;
   measuring a distance between one of the superior ledge member and at least one of the acromion or coracoid process;
   coupling at least one spacer between the superior ledge member and at least one of an acromion or coracoid process of a patient;
   passing a fastener through a first aperture in the superior ledge member, a second aperture in the spacer and into bone;
   coupling the fastener to at least one of an acromion or coracoid process;
   coupling a bearing to the glenoid base after coupling the glenoid base to the prepared glenoid surface, said bearing having a superior ledge positioned adjacent to the superior ledge member.

7. The method according to claim 6 wherein coupling at least one spacer is coupling a first spacer to the acromion.

8. The method according to claim 6 wherein coupling a bearing occurs after passing a fastener through a first aperture.

9. The method according to claim 6 wherein coupling a glenoid base to a prepared glenoid includes passing a fastener through an aperture defined in the glenoid base.

10. The method according to claim 1 wherein fixing a bearing component to the glenoid base comprises coupling a bearing superior ledge adjacent the superior ledge portion.

11. The method according to claim 1 wherein fixing a bearing component to the glenoid base comprises coupling a bearing locking mechanism to a locking feature.

12. The method according to claim 1 further comprising passing a fastener through a slot defined in the support tray into the glenoid surface.

13. The method according to claim 12 further comprising translating the L-shaped glenoid base on the prepared glenoid surface to position the superior ledge member against one of the acromion or coracoid process.

14. The method according to claim 6 further comprising disposing a locking mechanism between the bearing and the L-shaped glenoid base.

15. The method according to claim 13 wherein the locking mechanism is one of a snap ring or a fixation member.

* * * * *

UNITED STATES PATENT AND TRADEMARK OFFICE
CERTIFICATE OF CORRECTION

| | |
|---|---|
| PATENT NO. | : 7,959,680 B2 |
| APPLICATION NO. | : 11/346543 |
| DATED | : June 14, 2011 |
| INVENTOR(S) | : Kevin T. Stone et al. |

It is certified that error appears in the above-identified patent and that said Letters Patent is hereby corrected as shown below:

Column 2, Line 32, "at one more coupling mechanisms" should be --at least one more coupling mechanism.--

Column 3, Line 64, "(now shown)" should be --(not shown)--

Column 5, Line 10, "defined" should be --define--

Column 7, Line 41, After "bone" insert --;--

Signed and Sealed this
Sixteenth Day of August, 2011

David J. Kappos
*Director of the United States Patent and Trademark Office*